(12) United States Patent
Chen

(10) Patent No.: US 6,541,659 B1
(45) Date of Patent: Apr. 1, 2003

(54) PROCESS FOR ACYL SUBSTITUTION OF ANHYDRIDE BY VANADYL SALT CATALYST

(75) Inventor: Chien-Tien Chen, Taipei (TW)

(73) Assignee: National Taiwan Normal University, Taipei (TW)

( * ) Notice: Subject to any disclaimer, the term of this patent is extended or adjusted under 35 U.S.C. 154(b) by 0 days.

(21) Appl. No.: 10/115,546

(22) Filed: Apr. 2, 2002

(51) Int. Cl.[7] .............................. C07C 69/02; B01J 21/00

(52) U.S. Cl. .................. 560/231; 502/100; 502/103; 502/151; 502/153; 502/154

(58) Field of Search ................. 560/231; 502/100, 502/103, 151, 153, 154

(56) References Cited

PUBLICATIONS

Klasek et al, Chemical Papers, (1997) 51 (2) pp. 111–116 as described in Chemical Abstract vol. 127 num 135436.*
Lee et al, Bull. Korean Chem. Soc. (1988) 9 (6) pp. 362–364, as described in Chemical Abstract, vol. 110, No. 204627.*
Chem Abrst. vol. 110, No. 204627 Lee et al.*
Chem. Abst. vol. 127 No. 135436 Klasek et al.*

* cited by examiner

*Primary Examiner*—Alan L. Rotman
*Assistant Examiner*—Héctor M Reyes
(74) *Attorney, Agent, or Firm*—Morgan & Finnegan, LLP

(57) ABSTRACT

A process for acyl substitution of an anhydride with an active-hydrogen-containing compound includes reacting the anhydride with the active-hydrogen-containing compound in the presence of a vanadyl salt catalyst to obtain a high yield of acyl substitution reaction product with high chemoselectivity.

10 Claims, No Drawings

PROCESS FOR ACYL SUBSTITUTION OF ANHYDRIDE BY VANADYL SALT CATALYST

BACKGROUND OF THE INVENTION

1. Field of the Invention

The invention relates to a process for acyl substitution of an anhydride with an active-hydrogen-containing compound, more particularly to a process for acyl substitution of an anhydride with an active-hydrogen-containing compound in the presence of a vanadyl salt catalyst so as to obtain a high yield of acyl substitution reaction product with high chemoselectivity.

2. Description of the Related Art

The acylations of alcohols, amines and thiols are important and commonly used transformations in organic synthesis. In these reactions, acid halides or anhydrides are often employed as the acyl source in basic media or in the presence of Lewis base or acid catalysts. In the past, trimethylsilyl (TMS) and metal triflates, such as indium, scandium, copper, and bismuth triflates, have been found to be effective in catalyzing the acylation of alcohols with anhydrides. However, only a few of them have been studied with more extensive species of anhydrides, and substrates bearing acid-sensitive groups, such as acetonide and allyl, might not be fully compatible. Moreover, most of these catalysts have encountered some disadvantages. For example, the acylation of allyl alcohols (such as cinnamyl alcohol) catalyzed by scandium triflate would produce rearranged by-products. The acylation catalyzed by trimethylsilyl triflate should be operated at a temperature of 0° C. or less so as to suppress the hydrolysis of the functional groups on the substrates. In addition, the actual role of the aforementioned catalysts in the catalytic pathway was not fully understood. In this application triflate refers to trifluoromethanesulfonate.

Notably, the preparation of metal triflates often require direct mixing of metal oxides with excess hot triflic acid (trifluoromethane sulfonic acid). The unavailability of complete removal of triflic acid from the metal triflates will diminish the value of the metal triflate as a catalyst because it might affect the overall catalytic activity in the acylation process. In this context, new mild and neutral catalysts, which can achieve general nucleophilic acyl substitution of anhydrides with protic nucleophiles, remain in great demand.

The value of vanadium-containing compounds as a catalyst in synthesis has been widely studied and assessed. Among them, oxovanadium (IV) (vanadyl) compounds were normally treated as pre-catalysts of the corresponding Vanadium (V) species. However, synthetic reactions and pathways that are directly catalyzed by vanadyl species were rarely studied in contrast. Togni in organometallics, 1990 reported the use of camphor-derived vanadyl bis (1,3-diketonato) complexes as Lewis acid catalysts for asymmetric Diels-Alder reactions between Danishefsky dienes and aldehydes. Although a concerted pathway was suggested in the report, the potential amphoteric characteristic of the V=O unit (i.e., $^+$V—O$^-$) which could.be conducive to a stepwise, push-pull type mechanism was not taught. Namely, the (partial) positively charged V in the V=O unit is a Lewis acid which is sufficient to activate the carbonyl oxygen of an aldehyde. In the meantime, the (partial) negatively charged O in the V=O unit serves as a Lewis base to activate an enol silane and to permit dissociation of the silyl group concomitantly.

SUMMARY OF THE INVENTION

Therefore, the object of the present invention is to provide a process for acyl substitution of an anhydride with an active-hydrogen-containing compound that is devoid of the aforesaid drawbacks of the prior art.

Accordingly, the process for acyl substitution of an anhydride with an active-hydrogen-containing compound includes reacting the anhydride with the active-hydrogen-containing compound in the presence of a vanadyl salt catalyst so as to obtain a high yield of acyl substitution reaction product with high chemoselectivity.

DETAILED DESCRIPTION OF THE PREFERRED EMBODIMENTS

In the process according to this invention, the anhydride is reacted with the active-hydrogen-containing compound in the presence of a vanadyl salt catalyst.

The vanadyl salt catalyst has the following formula:

$$(VO)X_2,$$

wherein $X_2$ is selected from the group consisting of $(OTf)_2$, $SO_3$-aryl, $SO_4$, $(acac)_2$, $(CH_3CO_2)_2$, $(F)_2$, $(Cl)_2$, $(Br)_2$, $(I)_2$, $Al_2O_4$, $(N_3)_2$, $SbF_6$, $HPO_4$, $MoO_4$, $(NbO_3)_2$, $(NO_3)_2$, $C_2O_4$, $(ClO_4)_2$, $SeO_4$, $Pt(CN)_4$, $TiO_3$, $WO_4$, and $ZrO_3$.

The active-hydrogen-containing compound has the following formula:

$$(R^1)_m\text{—}RH_n\text{—}C\text{—}YH$$

wherein

Y is selected from the group consisting of O, NH and S;

R is hydrocarbylene group;

each of $R^1$ is independently selected from the group consisting of alkene moiety, ester moiety, lactone moiety, ketone moiety, imide moiety, acetonide moiety, and lactol moiety;

m is 0, 1, 2 or 3;

n is 0, 1, 2, or 3; and m+n=3

"OTf" represents triflate or trifluoromethane sulfonate.

The anhydride typically has the following formula:

$$(R'CO)_2O$$

wherein each of R' is independently selected from the group consisting of acyclic aliphatic moiety, cyclic aliphatic moiety and aromatic moiety.

A proposed reaction mechanism between an amphoteric vanadyl salt catalyst and an anhydride in the catalytic acylation of an alcohol is illustrated in the following Scheme 1:

Scheme 1:

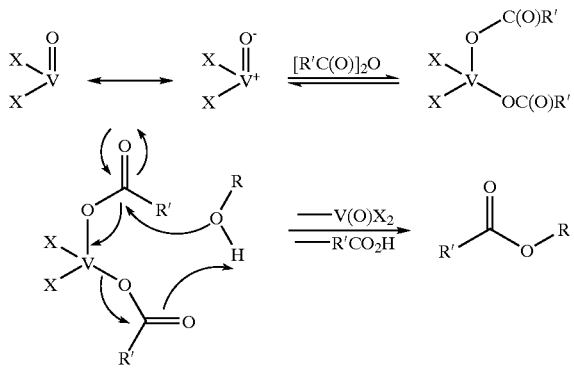

As shown in the above Scheme 1, a protic nucleophile (e.g., the alcohol in the scheme) may add to one of the two alkanoates in the adduct with concomitant elimination of an alkanoic acid to regenerate the vanadyl salt catalyst.

The most preferred vanadyl triflate catalyst can be produced either by reacting vanadyl sulfate with barium triflate or by reacting vanadium oxide and an excess of triflic acid in a suitable solvent.

The process according this invention is useful for the acylation required in the process for preparing sun-screen lotion and surfactant, such as the acylation of sorbitol, glycerin, fatty acid or N,N-dimethyl benzoic acid. The process according to this invention is also useful for the acylation of saccharides and the synthesis of peptides.

The following examples further illustrate the preferred embodiments of the invention, but are not to be construed as limiting.

EXAMPLES:

Example 1

The Preparation of Vanadyl Triflate [V(O) (OTf)$_2$-x(H$_2$O)]

Vanadyl sulfate (V(O)SO$_4$.3H$_2$O) (342 mg, 2.1 mmole) was added into a two-neck flask (50 ml, vacuum-dried), and is then dissolved with methanol (2 ml). Barium triflate solution in methanol (2M, 2 ml) was added at room temperature and mixed homogeneously for 30 mins. Barium sulfate precipitate was formed. The precipitate was filtered via diatomaceous earth, and the filtrate was-collected. The solvent remained in the filtrate was removed under vacuum (120° C., 4 hrs). Dark blue solid (622 mg, yield: 85%) was obtained. The obtained vanadyl triflate can be used directly for the acylation.

Example 2

The Preparation of Vanadyl Acetate [V(O) (OAc)$_2$-x(H$_2$O)]

In a dry 5-mL, two-necked, round-bottomed reaction flask, vanadyl sulfate trihydrate (114.0 mg, 0.53 mmol) was placed, followed by addition of methanol (1 mL). A solution of Ba(OAc)$_2$ (130.3 mg, 0.51 mmol) in methanol (1 mL) was added to the reaction flask at ambient temperature. After 30 min of stirring, precipitation of barium sulfate was observed, which was filtered off over a short pad of dry Celite. The filtrate was concentrated and dried in vacuo at 120° C. for 4 hours, and 109.5 mg (90% yield) of vanadyl acetate as bluish solids was obtained.

Example 3

The Preparation of Vanadyl Chloride [V(O) Cl$_2$-x(H$_2$O)]

In a dry 5-mL, two-necked, round-bottomed reaction flask, vanadyl sulfate trihydrate (114.0 mg, 0.53 mmol) was placed, followed by addition of aqueous methanol (MeOH/H$_2$O, 1/0.3 mL). A solution of BaCl$_2$-2H$_2$O (122.1 mg, 0.50 mmol) in methanol (1 mL) was added to the reaction flask at ambient temperature. After 30 min of stirring, precipitation of bariumsulfate was observed, which was filtered off over a short pad of dry Celite. The filtrate was concentrated and dried in vacuo at 120° C. for 4 hours, and 86.4 mg (90% yield) of vanadyl chloride as pale purple solids was obtained.

Example 4

The Preparation of Vanadyl Azide [V(O) (N$_3$)$_2$-x(H$_2$O)]

In a dry 5-mL, two-necked, round-bottomed reaction flask, vanadyl sulfate trihydrate (114.0 mg, 0.53 mmol) was placed, followed by addition of methanol (1 mL). A solution of Ba(N$_3$)$_2$ (112.5 mg, 0.51 mmol) in methanol (1 mL) was added to the reaction flask at ambient temperature. After 30 min of stirring, precipitation of barium sulfate was observed, which was filtered off over a short pad of dry Celite. The filtrate was concentrated and dried in vacuo at 120° C. for 2 hours, and 91.5 mg (88% yield) of vanadyl azide as brownish solids was obtained.

Example 5

The Preparation of Vanadyl Hexafluoroantimonate [V(O) (SbF$_6$)$_2$-x(H$_2$O)]

In a dry 5-mL, two-necked, round-bottomed reaction flask, vanadyl chloride trihydrate (88.0 mg, 0.50 mmol) was placed, followed by addition of THF (2 mL). A solution of AgSbF$_6$ (343.5 mg, 1.0 mmol) in THF (1 mL) was added to the reaction flask at ambient temperature. After 2 hours of stirring, precipitation of silver chloride was observed, which was filtered off over a short pad of dry Celite. The filtrate was concentrated and dried in-vacuo at 120° C. for 4 hours, and 254.6 mg (86% yield) of vanadyl hexafluoroantimonate as redish brown solids was obtained.

Example 6

The Preparation of Vanadyl Perchlorate [V(O) (ClO$_4$)$_2$-x(H$_2$O)]

In a dry 5-mL, two-necked, round-bottomed reaction flask, vanadyl sulfate trihydrate (114.0mg, 0.53 mmol) was placed, followed by addition of methanol (1 mL). A solution of Ba(ClO$_4$)$_2$ (171.5 mg, 0.51 mmol) in methanol (1 mL) was added to the reaction flask at ambient temperature. After 30 min of stirring, precipitation of barium sulfate was observed, which was filtered off over a short pad of dry Celite. The filtrate was concentrated and dried in vacuo at 120° C. for 2 hours, and 130.6 mg (80% yield) of vanadyl perchlorate as brownish solids was obtained.

Example 7

The Preparation of Vanadyl Tetracyanoplatinate [V(O)Pt(CN)$_4$-x(H$_2$O)]

In a dry 5-mL, two-necked, round-bottomed reaction flask, vanadyl sulfate trihydrate (114.0 mg, 0.53 mmol) was placed, followed by addition of methanol (1 mL). A solution of BaPt(CN)$_4$-xH$_2$O (222.5 mg, 0.51 mmol) in methanol (1 mL) was added to the reaction flask at ambient temperature. After 30 min of stirring, precipitation of barium sulfate was observed, which was filtered off over a short pad of dry Celite. The filtrate was concentrated and dried in vacuo at 120° C. for 4 hours, and 190.8 mg (89% yield) of vanadyl tetracyanoplatinate as brownish solids was obtained.

Example 8

The Preparation of Vanadyl Titanate [V(O)TiO$_3$-x(H$_2$O)]

In a dry 5-mL, two-necked, round-bottomed reaction flask, vanadyl sulfate trihydrate (114.0 mg, 0.53 mmol) was placed, followed by addition of methanol (1 mL). A solution of BaTiO$_3$ (118.9 mg, 0.51 mmol) in methanol (1 mL) was added to the reaction flask at ambient temperature. After 30 min of stirring, precipitation of barium sulfate was observed, which was filtered off over a short pad of dry Celite. The filtrate was concentrated and dried in vacuo at 120° C. for 4 hours, and 101.9 mg (92% yield) of vanadyl titanate as bluish solids was obtained.

Example 9

Acetylation Reaction of Vanadyl Salt Catalysts

In this example, four different species of vanadyl salt catalysts were tested in mediating the acetylation of 2-phenylethanol.

Entry 1

Acetylation Reaction with Vanadyl Acetylacetonate

In a dry 50-mL, two-necked, round-bottomed flask, vanadyl acetylacetonate (13.7 mg, 0.05 mmol) in 3 mL of anhydrous CH$_2$Cl$_2$ was placed. To the above solution, acetic anhydride (153.1 mg, 141.5 µL, 1.5 mmol) was slowly added at ambient temperature. After about 10 min, a solution of 2-phenylethanol (122 mg, 119.3 µL, 1.0 mmol) in CH$_2$Cl$_2$ (2 mL) was slowly added to the above dark green solution, and the reaction mixture was stirred for 5 hours. After completion of the reaction as monitored by TLC, the reaction mixture was quenched with cold, saturated aqueous NaHCO$_3$ solution (5 mL). The resulting separated organic layer was washed with brine, dried (MgSO$_4$), filtered, and evaporated. The crude product was purified by column chromatography on silica gel to yield 139.4 mg of 2-phenethyl acetate (85%) as colorless oil. The substrate, reaction time, and yield of this test are summarized in Entry 1 of the following Table 1.

Entry 2

Acetylation Reaction with Vanadyl Chloride

In a dry 50-mL, two-necked, round-bottomed flask, vanadyl chloride (1.9 mg, 0.01 mmol) in 3 mL of anhydrous CH$_2$Cl$_2$ was placed. To the above solution, acetic anhydride (153.1 mg, 141.5 µL, 1.5 mmol) was slowly added at ambient temperature. After about 10 min, a solution of 2-phenylethanol (122 mg, 119.3 µL, 1.0 mmol) in CH$_2$Cl$_2$ (2 mL) was slowly added to the above brownish solution, and the reaction mixture was stirred for 7.5 hours. After completion of the reaction as monitored by TLC, the reaction mixture was quenched with cold, saturated aqueous NaHCO$_3$ solution (5 mL). The resulting separated organic layer was washed with brine, dried (MgSO$_4$), filtered, and evaporated. The crude product was purified by column chromatography on silica gel to yield 154.2 mg of 2-phenethyl acetate (94%) as colorless oil. The substrate, reaction time, and yield of this test are summarized in Entry 2 of the following Table 1.

Entry 3

Acetylation Reaction with Vanadyl Sulfate

In a dry 50-mL, two-necked, round-bottomed flask, vanadyl sulfate (8.2 mg, 0.05 mmol) in 3 mL of anhydrous CH$_3$CN was placed. To the above mixture, acetic anhydride (153.1 mg, 141.5 µL, 1.5 mmol) was slowly added at ambient temperature. After about 10 min, a solution of 2-phenylethanol (122 mg, 119.3 µL, 1.0 mmol) in CH$_3$CN (2 mL) was slowly added to the above bluish solution with residual suspended vanadyl sulfate, and the reaction mixture was stirred for 24 hours. After completion of the reaction as monitored by TLC, the reaction mixture was quenched with cold, saturated aqueous NaHCO$_3$ solution (5 mL). The resulting separated organic layer was washed with brine, dried (MgSO$_4$), filtered, and evaporated. The crude product was purified by column chromatography on silica gel to yield 150.9 mg of 2-phenethyl acetate (92%) as colorless oil. The substrate, reaction time, and yield of this test are summarized in Entry 3 of the following Table 1.

Entry 4

Acetylation Reaction with Vanadyl Triflate

Vanadyl triflate was first heated in refluxing trifluoroacetic anhydride (R'=CF$_3$) for 12 hours and then concentrated. The resultant adduct was treated with a stoichiometric amount of 2-phenylethanol in CH$_2$Cl$_2$ for 3 hours. The corresponding 2-phenethyl trifluoroacetate was isolated. The substrate, reaction time, and yield of this test are summarized in Entry 6 of the following Table 1.

The substrates, reaction times, and yields of the test of other entries are summarized in the following Table 1.

TABLE 1

Catalytic Acylations of 2-Phenylethanol with Various Anhydrides in the Presence of Various Species of Vanadyl Salt Catalysts

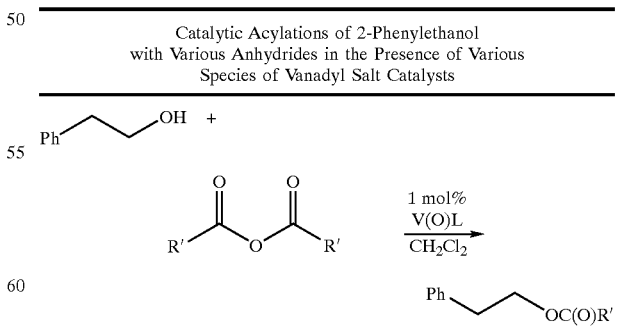

| Entry | V(O)L | Anhydride (R') | time (h) | Yield,[a] % |
|---|---|---|---|---|
| 1 | V(O)(acac)$_2$[b,c] | CH$_3$ | 5 | 85 |
| 2 | V(O)Cl$_2$ | CH$_3$ | 7.5 | 94 |

TABLE 1-continued

Catalytic Acylations of 2-Phenylethanol with Various Anhydrides in the Presence of Various Species of Vanadyl Salt Catalysts

|   | | | | |
|---|---|---|---|---|
| 3 | V(O)SO$_4$[c,d] | CH$_3$[e] | 24 | 92 |
| 4 | V(O)(OTf)$_2$ | CH$_3$ | 0.5 | 98 |
| 5 | V(O)(OTf)$_2$[f] | CH$_3$ | 0.75 | 98 |
| 6 | V(O)(OTf)$_2$ | CF$_3$ | 3 | 98 |
| 7 | V(O)(OTf)$_2$ | i-Pr | 1 | 98 |
| 8 | V(O)(OTf)$_2$ | tert-Bu | 11 | 99 |
| 9 | V(O)(OTf)$_2$ | tert-BuO | 28 | 95 |
| 10 | V(O)(OTf)$_2$ | Ph | 26 | 92 |
| 11 | V(O)(OTf)$_2$ | succinic | 42 | 93 |
| 12 | V(O)(OTf)$_2$ | phthalic | 96 | 75[g] |

[a]Isolated yields.
[b]Acetylacetonate.
[c]Five mol % catalyst was used.
[d]The trihydrate was used.
[e]CH$_3$CN was used as solvent.
[f]Catalyst was recovered from aqueous layer and reused for 5 consecutive runs.
[g]Diphenethyl ester was isolated in 16%.

Trials with 5 mol % of vanadyl acetylacetonate (VO(acac)$_2$) and vanadyl sulfate were effective to complete the acetylation at ambient temperature in the presence of 1.5 equiv. of Ac$_2$O in 5 and 24 hours, respectively.

Vanadyl chloride and triflate, which were prepared from vanadyl sulfate and suitable barium salts, were found to be much more reactive. Acetylation using 1 mol % of V(O)Cl$_2$ and V(O) (OTf)$_2$ with 1.5 equiv. of Ac$_2$O in CH$_2$Cl$_2$ was completed in 7.5 and 0.5 hours, respectively, leading to phenethyl acetate with at least 94% yield. It should be noted that the corresponding VCl$_3$ and V(OTf)$_2$ are catalytically inactive, supporting the role of the V=O unit in the vanadyl catalysts. In addition, there is no need for chromatographic purification with the acetylation protocol since the remaining acetic anhydride and vanadyl triflate can be readily removed by direct aqueous wash. More importantly, V(O)(OTf)$_2$ is fully compatible with water. It can be recovered from the concentrate of the aqueous layer and reused for at least five consecutive runs with similar catalytic activity.

As shown in Table 1, besides acetic anhydride, the catalytic system is amenable to acyclic, cyclic, aliphatic and aromatic anhydrides. In general, the more hindered the anhydride, the slower the acylation rate. (i.e., CH$_3$>i-Pr>t-Bu; refer to entries 4, 7 and 8 in Table 1). Acylation with an aromatic anhydride (e.g., R-Ph in entry 10 of Table 1) is up to 50 times slower than those with aliphatic anhydrides (entries 4 and 6–8 in Table 1). Acylation with di-tert-butyl dicarbonate also proceeds well and with a rate similar to that of benzoylation (entry 9 in Table 1). Cyclic anhydrides, such as succinic and phthalic anhydride, are the least reactive (entries 11 and 12 in Table 1).

Example 10

With the optimal catalyst-vanadyl triflate on hand, nucleophilic acyl substitutions of both acetic and pivalic anhydride (representing two steric extremes) with protic nucleophiles (e.g., alcohols, amines, and thiols) of varying steric and electron transfer demands were tested in this example. The substrates, reaction times, and yields of the test in this example are summarized in the following Table 2.

TABLE 2

Vanadyl Triflate-Catalyzed Acetylation and Pivalation of Alcohols, Amines, and Thiols

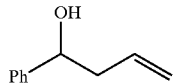

R = Me, C(CH$_3$)$_3$

| Entry | substrate[a] | time, h | yield,[b] % |
|---|---|---|---|
| 1 | Ph(CH$_2$)$_2$OH | 0.5 (11[c]) | 99 (99) |
| 2 | PhCH=CHCH$_2$OH | 3.5[d] (72[e]) | 98 (85) |
| 3 | 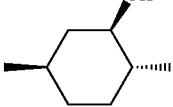 | 10 (24) | 97 (97) |
| 4 | 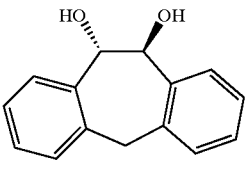 | 1 (96[f]) | 97 (84) |
| 5 | 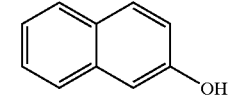 | 1 (5[g]) | 98 (95) |
| 6 | 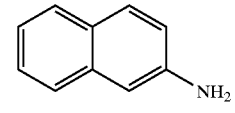 | 5 (36) | 99 (99) |
| 7 | 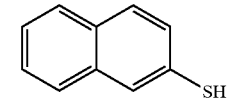 | 8 (42) | 99 (99) |
| 8 |  | 40 (96) | 99 (98) |
| 9 | (i-Pr)$_2$NH | 3 | 97 |
| 10 | tert-BuSH | 12 (24) | 99 (95) |

[a]1.5 equiv of anhydride was used unless otherwise stated.
[b]Isolated yields and characterized spectroscopically.
[c]The data in parentheses correspond to pivalations.
[d]Two equiv of anhydride was used.
[e]Three equiv of anhydride was used.
[f]THF was used as solvent.
[g]Toluene was used as solvent.

In almost all cases, except in the pivalations of cinnamyl alcohol (85%) and menthol (84%), the chemical yields of acylation were at least 95%. In general, acetylations proceed much faster than the corresponding pivalations. Acylations go smoothly with primary, secondary, and acid-sensitive allylic and benzylic alcohols. No trace of allylic or pinacol rearrangement by-products was observed in the case of cinnamyl alcohol and 10,11-dihydroxy-dibenzosuberane (entries 2 and 5 in Table 2). Tertiary alcohols, such as tert-butyl alcohol and trityl alcohol, were inactive. Nevertheless, the corresponding tert-butanethiol was fairly reactive (entry 10 in Table 2). Aromatic alcohols, amines and thiols (e.g., 2-hydroxy, 2-amino, and 2-thio-naphthalenes) were amenable to acylations in essentially quantitative yields (entries 6–8 in Table 2).

Example 11

Acetylation and/or pivalation of various functionalized substrates were tested in this example. The substrates, reaction times and yields of the test in this example are summarized in the following Table 3.

TABLE 3

Acetylation and/or Pivalation of Functionalized Substrates

| Entry | substrate[a] | time, h | yield,[b] % |
|---|---|---|---|
| 1 | (cyclohexenyl with OH and OC(O)Ph) | 0.5 (48[c]) | 99 (99) |
| 2 | Ph-CH(OH)-C(O)OMe | 2 (3) | 96 (95) |
| 3 | t-Bu-CH(NH$_2$)-C(O)OMe | 0.5[d] (1.5) | 100 (85) |
| 4 | Ph-CH(OH)- γ-butyrolactone | 12 (24) | 95 (95) |
| 5 | Ph-CH(OH)-cyclohexanone | 6 (12) | 100 (100) |
| 6 | (uridine) | 96[e] | 90 |
| 7 | (diacetone sugar) | 49[f] | 75 |
| 8 | (disaccharide) | 60[e,g] | 85 |

TABLE 3-continued

Acetylation and/or Pivalation of Functionalized Substrates

| Entry | substrate[a] | time, h | yield,[b] % |
|---|---|---|---|
| 9 | β-cyclodextrin | 96[g] | 90 |
| 10 | [naphthalene-2,3-diyl with CH₂OH* and OH] | 3[h] (48) | 95 (96) |
| 11 | [t-Bu, H₂N*, OH structure] | 2[h,i] (15) | 60[i] (97) |

[a]1.5 equiv of anhydride was used unless otherwise stated.
[b]Isolated yields and characterized spectroscopically.
[c]The data in parentheses correspond to pivalations.
[d]Two equiv of anhydride was used.
[e]Three equiv of anhydride was used.
[f]Carried out at −5° C.
[g]No solvent was used.
[h]Asterisk signifies the reactive site.
[i]For effective mono-acylation, 0.95 equiv of anhydride was used.
[j]Di-acetylated product was isolated 10% yield.

As shown in Table 3, the acylation protocol is tolerant to protic nucleophiles bearing functional groups, such as alkene, ester, lactone, ketone, imide, acetonide and lactol (entries 1–9 in Table 3). Their acylations proceeded smoothly with 75–100% yields. Side reactions, such as oxidation (dehydrogenation) and dehydration, were not observed in the case of α-hydroxy, α-amino esters (entries 2 and 3 in Table 3), and β-hydroxy esters and ketones (entries 4 and 5 in Table 3). No trace of the glycosidic C-O cleavage was observed in the acetylation of diacetone-D-glucose (entry7 in Table 7) at −5° C., although 22% of acetylation at the primary hydroxy group with concomitant migration of the acetonide-unit could not be prevented.

The high catalytic efficacy of vanadyl triflate was further demonstrated in the peracetylations of polyhydroxyl molecules, such as uridine, lactose, and cylcodextrin (21 OH groups). In all cases, reactions go to completion in acetic acid or in neat acetic anhydride, albeit with longer reaction time (2.5–4 days). By taking advantage of the differential reactivity between nucleophiles, chemoselective acylation of 3-hydromethyl-2-naphthol could be carried out. Its primary hydoxyl group is acylated with complete chemoselectivity and with at least 95% yield (entry 10 in Table 3). Acetylation of tert-leucinol at the sterically hindered amino moiety was moderately selective. The corresponding N-acetylated product was furnished with 60% yield. Nevertheless, the analogous N-pivalation proceeded with complete selectivity (97%).

Example 12

Since benzoic anhydride is the least reactive acyclic anhydride, one may carry out acylation directly with fatty acid in the presence of benzoic anhydride.

In this example, the in-situ-generated mixed anhydride acts as the real acylation reagent. The reaction of 1-phenethyl-3-buten-1-ol with a mixture of oleic acid and benzoic anhyride and, the reaction of Fmoc-L-leucine with methyl t-tert-leucinate are shown in the following Scheme 2. As shown in the Scheme 2, 1-phenethyl-3-buten-1-ol was treated with a mixture of oleic acid and benzoic anhyride (1.1 equiv.) in $CH_2Cl_2$ with 5 mol % of vanadyl triflate for 2 hours. The resultant oleate was produced smoothly with 82% yield. The mixed anhydride technique can also be applied to dipeptide synthesis, as illustrated in the direct coupling of Fmoc-L-leucine and methyl t-tert-leucinate with 93% yield.

Scheme 2
Acylations with Mixed-Anhydride
Aproaches in Oleate and Dipeptide Syntheses

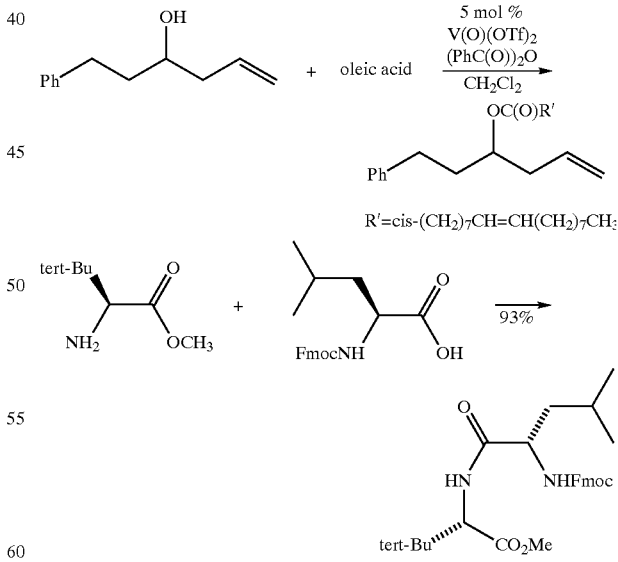

Example 13

It was found that amines, thiols, and primary and aromatic alcohols are amenable to benzoylations. However, benzoylations of secondary alcohols are rather limited and require harsher reaction conditions. The substrates, reaction times and yields of the test for the benzoylation of alcohols, amines and thiols are summarized in the following Table 4. As shown in Table 4, the only workable secondary alcohol is shown in entry 8 of Table 4, which underwent benzoylation at 50° C. with 52% yield.

TABLE 4

Benzoylation of alcohols, amines and thiols

| Entry | Substrate[a] | Time, h | yield,[b] % |
|---|---|---|---|
| 1 | Ph(CH$_2$)$_2$OH | 26 | 92 |
| 2 | OH (2-naphthol) | 80 | 99 |
| 3 | 1-naphthol | 96 | 99 |
| 4 | 2-naphthylamine (NH$_2$) | 96 | 99 |
| 5 | (i-Pr)$_2$NH | 18 | 95 |
| 6 | 2-naphthalenethiol (SH) | 96 | 96 |
| 7 | Tert-BuSH | 36 | 97 |
| 8 | cyclohexenyl (OH, OC(O)Ph) | 72[c] | 52 |
| 9 | t-Bu, H$_2$N, OMe (amino acid ester) | 0.5 | 100 |
| 10 | 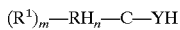 naphthalene-diol-CH$_2$OH* | 60[d] | 83 |
| 11 | t-Bu, H$_2$N*, OH* | 6[d,e] | 73 |

[a]1.5 equiv of anhydride was used unless otherwise stated.
[b]Isolated yields and characterized spectroscopically.
[c]Carried out in THF at 50° C. and with 2 mol % catalyst.
[d]Asterisk signifies the reactive site.
[e]For effective mono-acylation, 0.95 equiv of anhydride was used.

Example 14

To support the mechanistic proposal shown in aforesaid Scheme I, vanadyl triflate was first heated in refluxing trifluoroaceic anhydride (R'=CF$_3$) for 12 hours and then concentrated. The resultant adduct was treated with a stoichiometric amount of 2-phenylethanol in CH$_2$Cl$_2$ for 3 hours. The corresponding 2-phenethyl trifluoroacetate was isolated with 87% yield.

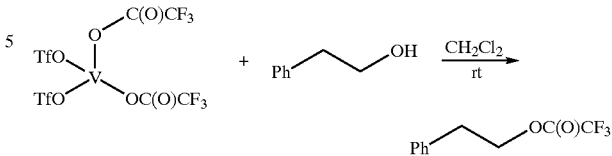

In view of the aforesaid, the vanadyl catalyst has been demonstrated to exhibit amphoteric catalytic behavior in nucleophilic acyl substitutions with various anhydrides, and thus represents a new type of water-tolerant metal salt catalyst. The acylation protocol allows for chemoselective acylation and tolerates many structural and substrate variations. Mixed anhydride technique allows for acylations with commercially unavailable anhydrides.

While the present invention has been described in connection with what is considered the most practical and preferred embodiments, it is understood that this invention is not limited to the disclosed embodiments but is intended to cover various arrangements included within the spirit and scope of the broadest interpretation so as to encompass all such modifications and equivalent arrangements.

I claim:

1. A process for acyl substitution of an anhydride with an active-hydrogen-containing compound, comprising reacting said anhydride with said active-hydrogen-containing compound in the presence of a vanadyl salt catalyst, wherein said vanadyl salt catalyst has the following formula:

$$(VO)X_2,$$

wherein $X_2$ is selected from the group consisting of (OTf)$_2$, SO$_3$-aryl, SO$_4$, (acac)$_2$, (CH$_3$CO$_2$)$_2$, (F)$_2$, (Cl)$_2$, (Br)$_2$, (I)$_2$, Al$_2$O$_4$, (N$_3$)$_2$, SbF$_6$, HPO$_4$, MoO$_4$, (NbO$_3$)$_2$, (NO$_3$)$_2$, C$_2$O$_4$, (ClO$_4$)$_2$, SeO$_4$, Pt(CN)$_4$, TiO$_3$, WO$_4$, and ZrO$_3$.

2. The process as claimed in claim 1, wherein said active-hydrogen-containing compound has the following formula:

$$(R^1)_m\text{—}RH_n\text{—}C\text{—}YH$$

wherein
Y is selected from the group consisting of O, NH and S;
R is hydrocarbylene group;
each of $R^1$ is independently selected from the group consisting of alkene moiety, ester moiety, lactone moiety, ketone moiety, imide moiety, acetonide moiety, and lactol moiety;
m is 0, 1, 2 or 3;
n is 0, 1, 2, or 3; and
m+n=3.

3. The process as claimed in claim 1, wherein said anhydride has following formula:

$$(R'CO)_2O$$

wherein each of R' is independently selected from the group consisting of acyclic aliphatic moiety, cyclic aliphatic moiety and aromatic moiety.

4. The process as claimed in claim 1, wherein said reacting step is performed in the presence of methylene chloride.

5. The process as claimed in claim 1, wherein said vanadyl salt catalyst is vanadyl triflate.

6. The process as claimed in claim 5, wherein said vanadyl triflate is produced by reacting vanadyl sulfate with barium triflate.

7. The process as claimed in claim 5, wherein said vanadyl triflate is produced by reacting vanadium oxide and an excess of triflic acid.

8. The process as claimed in claim 1, wherein said process is an acylation of at least one selected from the group consisting of sorbitol, glycerin, fatty acid, and N,N-dimethylbenzoic acid.

9. The process as claimed in claim 1, wherein said process is an acylation of saccharide.

10. The process as claimed in claim 1, wherein said process is a synthesis of peptide.

* * * * *